United States Patent [19]
Kasina et al.

[11] Patent Number: 5,399,710
[45] Date of Patent: Mar. 21, 1995

[54] PROTEIN LABELING REAGENTS

[75] Inventors: Sudhakar Kasina; Ananthachari Srinivasan, both of Kirkland; James Sanderson, Seattle; Alan R. Fritzberg, Edmonds, all of Wash.

[73] Assignee: NeoRx Corporation, Seattle, Wash.

[21] Appl. No.: 994,939

[22] Filed: Dec. 22, 1992

Related U.S. Application Data

[62] Division of Ser. No. 590,180, Sep. 28, 1990, Pat. No. 5,175,256.

[51] Int. Cl.$^6$ ............... C07D 487/04; C07D 207/38; C07C 101/04
[52] U.S. Cl. .................... 548/453; 548/517; 548/541; 548/544; 549/32; 549/33; 549/60; 549/62; 549/63; 536/4.1; 536/17.4; 536/17.6
[58] Field of Search .............. 548/400, 404, 453, 515, 548/517, 541, 544; 549/29, 54, 62, 68, 58, 60, 32, 33, 63; 530/391.1, 391.3, 391.5, 404, 408; 424/1.1; 536/4.1, 17.4, 17.6

[56] References Cited

U.S. PATENT DOCUMENTS

| | | | |
|---|---|---|---|
| 2,810,753 | 10/1957 | Bersworth | 562/557 |
| 3,240,799 | 3/1966 | Hageman et al. | 560/169 |
| 3,424,740 | 1/1969 | Weaver et al. | 548/546 |
| 3,429,871 | 2/1969 | Weaver et al. | 548/546 |
| 3,790,568 | 12/1974 | Kerwood et al. | 548/545 |
| 4,352,751 | 10/1982 | Wieder et al. | 530/409 |
| 4,479,930 | 10/1984 | Hnatowich | 424/1.1 |
| 4,504,462 | 3/1985 | Van Duzee et al. | 424/1.1 |
| 4,517,123 | 5/1985 | Iso et al. | 540/544 |
| 4,659,839 | 4/1987 | Nicolotti et al. | 548/546 |
| 4,709,052 | 11/1987 | Tomioka et al. | 548/548 |
| 4,734,498 | 3/1988 | Cooper | 540/364 |
| 4,883,862 | 11/1989 | Chervu et al. | 530/331 |
| 4,897,255 | 1/1990 | Fritzberg et al. | 424/1.1 |
| 5,175,256 | 12/1992 | Kasina et al. | 530/391.5 |

FOREIGN PATENT DOCUMENTS

| | | |
|---|---|---|
| 135160 | 3/1985 | European Pat. Off. |
| 241255 | 12/1986 | German Dem. Rep. |
| 2429784 | 1/1975 | Germany |

OTHER PUBLICATIONS

*Advanced Organic Chemistry=Reactions, Mechanisms, and Structure* second ed., J. March, McGraw-Hill Book Company, New York, St. Louis 1977 pp. 21–22.

Green et al (1981) in *Protective Groups in Organic Synthesis* John Wiley and Sons, NY, N.Y. pp. 204–209 and 216–217.

Lever et al., *Tetrahedron Letters*, vol. 29, No. 26, pp. 3219–3222, 1988 (printed in Great Britain), "Synthesis of a novel bifunctional chelate designed for labeling proteins with technetium-99m".

(List continued on next page.)

*Primary Examiner*—Kay K. A. Kim
*Attorney, Agent, or Firm*—Seed and Berry

[57] ABSTRACT

Novel labeling reagents are useful for radiolabeling proteins such as antibodies with radionuclide metals such as $^{99m}Tc$, $^{186}Re$, and $^{188}Re$. The reagents are of the following formula:

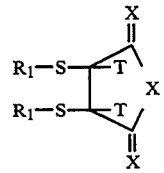

wherein:

each X is independently chosen from O, S, NH, or $NR_2$, wherein $R_2$ is a protecting group or an electron withdrawing group;

$R_1$ represents a protecting group, wherein each $R_1$ is a separate protecting group or the two $R_1$ symbols are taken together to represent a single protecting group; and each T is independently chosen from hydrogen, lower alkyl groups of from 1 to about 6 carbon atoms, electron withdrawing groups, and lower alkyl groups of from 1 to about 6 carbon atoms substituted with electron withdrawing group(s).

10 Claims, No Drawings

OTHER PUBLICATIONS

Boyd et al., *Int. J. Peptide Protein Res.*, 4, 1972, pp. 117–122, "N-acylsuccinimides as acylating agents for proteins: the selective acylation of lysine residues".

Medi-Physics, Inc. brochure for Product No. 4349, "MPI DMSA Kidney Reagent" Mar., 1989.

Blower et al., *J. Nucl. Med.*, Abstract No. 253, published May 1990, vol. No. 5, "Pentavalent rhenium-186 DMSA: A possible tumour therapy agent".

Kolasa and Miller, *J. Org. Chem.* 1986, 51, pp. 3055–3058, "A simple method for distinguishing optical isomers of chiral amines, hydroxylamines, amino acids, and peptides".

*Heterocyclic Compounds*, vol. 45, pp. 145–147 and 186.

Pierce Chemical Company Immunotechnology Catalog and Handbook, pp. E-14 and E-15 (1990).

Wey et al., Abstracts of Papers, Part 2, from the 200th Amer. Chem. Soc. National Meeting, Aug. 26–31, 1990, Abstract No. 66.

PROTEIN LABELING REAGENTS

CROSS REFERENCE TO RELATED APPLICATION

This application is a divisional application of Ser. No. 07/590,180, U.S. Pat. No. 5,175,256, filed Sep. 28, 1990.

BACKGROUND

Radiolabeled proteins such as antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradication of the undesired target cells. Alternatively a monoclonal antibody having a diagnostically effective radionuclide attached thereto may be administered, whereupon the radiolabeled antibody localizes on the target tissue. Conventional diagnostic procedures then may be used to detect the presence of the target sites within the patient.

One method for radiolabeling proteins such as antibodies involves attachment of radionuclide metal chelates to the proteins. Chelates having a variety of chemical structures have been developed for this purpose. The usefulness of such chelates is dependent upon a number of factors such as the stability of radionuclide binding within the chelate and the reactivity of the chelate with the desired protein. The efficiency of radiolabeling of the chelating compound to produce the desired radionuclide metal chelate also is important. Another consideration is the biodistribution of the radiolabeled antibody and catabolites thereof in vivo. Localization in non-target tissues limits the total dosage of a therapeutic radiolabeled antibody that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies.

SUMMARY OF THE INVENTION

The present invention provides chelating compounds useful as protein labeling reagents, methods for radiolabeling targeting molecules such as proteins using the reagents, and the resulting radiolabeled targeting proteins. The radiolabeled proteins of the present invention have use in various assays as well as in vivo diagnostic and therapeutic procedures. The protein may be a monoclonal antibody that binds to cancer cells, for example.

Compounds of the present invention include compounds of the formula:

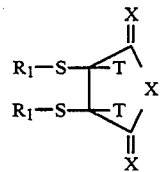

wherein:

each X is independently chosen from O, S, NH, or $NR_2$, wherein $R_2$ represents a substituent selected from protecting groups and electron withdrawing groups;

$R_1$ represents a protecting group, wherein each $R_1$ is a separate protecting group or the two $R_1$ symbols are taken together to represent a single protecting group; and each T is independently chosen from hydrogen, lower alkyl groups of from 1 to about 6 carbon atoms, electron withdrawing groups, and lower alkyl groups of from 1 to about 6 carbon atoms substituted with electron withdrawing group(s). Examples of suitable electron withdrawing groups are nitro, sulfonate, and carboxylic acid groups.

The compounds of formula I are reacted with proteins (to attach the compounds to the proteins) and radiolabeled. The resulting radiolabeled proteins lave diagnostic or therapeutic use, depending on the particular radionuclide employed.

Relatively fast kinetics are achieved during the radiolabeling reaction. In addition, the relatively stable binding of the radionuclide metal within the chelate is especially beneficial for in vivo use of the radiolabeled proteins.

Detailed Description of the Invention

The present invention provides chelating compounds useful as protein labeling reagents, methods for radiolabeling proteins using these reagents, and the resulting radiolabeled proteins having use in diagnostic or therapeutic procedures. The protein labeling reagents are of the following formula:

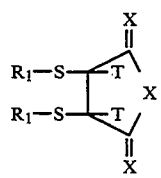

wherein:

each X is independently chosen from O, S, NH, or $NR_2$, wherein $R_2$ represents a substituent selected from protecting groups and electron withdrawing groups;

$R_1$ represents a protecting group, wherein each $R_1$ is a separate protecting group or the two $R_1$ symbols are taken together to represent a single protecting group; and each T is independently chosen from hydrogen, lower alkyl groups of from 1 to about 6 carbon atoms, electron withdrawing groups, and lower alkyl groups substituted with electron Withdrawing group(s).

The two T substituents preferably are identical (preferably, both are methyl groups, most preferably, both are hydrogen).

Representative examples of the compounds of formula (I) include, but are not limited to:

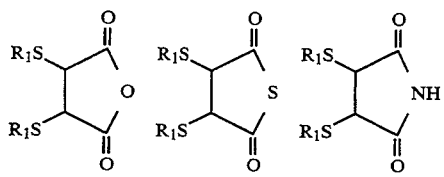

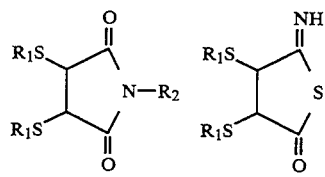

A particularly preferred compound of the present invention is:

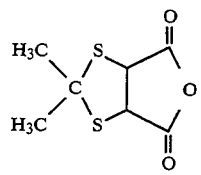

which also may be represented as:

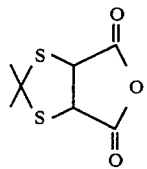

R₁ represents any suitable protecting group. A number of protecting groups, including but not limited to acyl, aryl, and alkyl groups, are known for use in protecting sulfur atoms. The protecting groups should be removable, either prior to or during the radiolabeling reaction. If removal of the protecting group(s) is desired after attachment of the reagent to a protein (but before radiolabeling), protecting group(s) removable under conditions that do not denature the protein should be chosen for use. The protecting groups represented by R₁ may be the same or different. In one embodiment of the invention, a single protecting group is attached to both sulfur atoms shown in formula I.

Among the preferred sulfur protecting groups are acetamidomethyl, hemithioacetal, and thioacetal protecting groups. Other suitable sulfur protecting groups are acyl type groups such as those of the formula

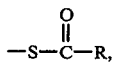

wherein the S is a sulfur atom of the chelating compound and R is an alkyl or aryl group. Examples are S-proprionyl, S-isobutyryl, S-benzoyl, and S-acetyl protecting groups.

An —S—R₁ group in which an acetamidomethyl protecting group is attached to the sulfur atom is represented by the following formula:

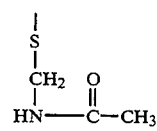

When hemithioacetal protective groups are used, each sulfur atom to be protected has a separate protective group attached to it, which together with the sulfur atom is a hemithioacetal group. The hemithioacetal groups contain a carbon atom bonded directly (i.e., without any intervening atoms) to a sulfur atom and an oxygen atom, i.e.,

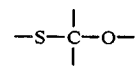

Preferred hemithioacetals generally are of the following formula:

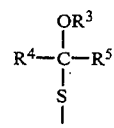

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to, the following R₁—S— groups:

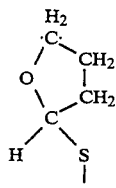 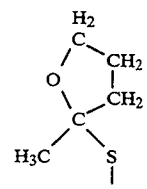

Tetrahydrofuranyl    2-methyl tetrahydrofuranyl

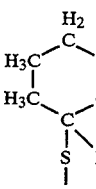 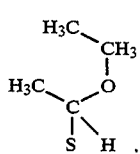

Tetrahydropyranyl    ethoxyethyl    2-methyl tetrahydropyranyl

Other hemithioacetal sulfur protecting groups include those derived from monosaccharides, e.g., those shown in the following S—R₁ groups:

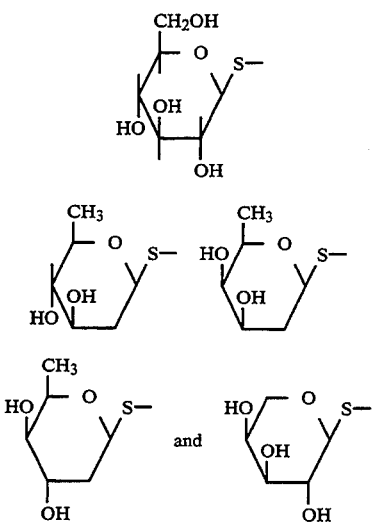

Thioacetals comprise a carbon atom bonded directly to two sulfur atoms, and may be represented as:

in the compounds of the present invention. Thus, time two $R_1$ symbols are taken together to represent a single protecting group. Preferred thioacetals may be represented by the following formula (where the two sulfur atoms are the sulfurs shown in formula I):

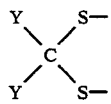

wherein each Y is independently chosen from hydrogen, lower alkyl groups (preferably methyl or ethyl), and lower alkoxy groups (preferably containing one or two carbon atoms), an aromatic ring, and an aromatic ring having an electron donating group (e.g., hydroxy, methoxy, or ethoxy group) bonded directly thereto.

Examples of thioacetals are as follows, wherein the two sulfur atoms shown in formula I are attached to a single protecting group, as follows:

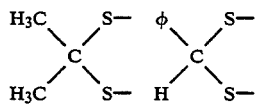

wherein φ represents an aromatic ring.

Other thioacetal protecting groups are shown in the examples section below, e.g., Example IX.

$R_2$ may represent any suitable protecting group or electron withdrawing group. Suitable electron withdrawing groups include, among others, nitro, sulfonate, and carboxylic acid groups. A number of nitrogen protecting groups are known and employed in the field of organic synthesis. It is to be understood that the term "protecting group" as used herein includes those substituted with electron withdrawing group(s). The electron withdrawing group renders the ring more susceptible to nucleophilic attack (e.g., by nucleophilic groups on proteins, thus attaching the reagent to the protein). Suitable $R_2$ groups include, but are not limited to, unsubstituted or substituted acyl or aryl groups, e.g., 2,4-dinitrophenyl, p-nitrophenyl, 2-chloro 4-nitrophenyl, or acetyl groups; unsubstituted or substituted lower alkyl groups, e.g., methyl; isonitriles; —$NO_2$; —CN; etc.

The compounds of formula I are useful as reagents for radiolabeling other molecules. The reagents generally are attached to the molecule to be radiolabeled prior to the radiolabeling reaction. The molecule should contain (or be modified to contain) a functional group such as a primary amine or hydroxyl that will react with the labeling reagent. The molecule may be any such molecule to be radiolabeled for use in in vitro assays, diagnostic or therapeutic procedures, or other such purpose.

In one embodiment of the invention, the molecule to be radiolabeled is a targeting molecule. The targeting molecule is any molecule that will serve to deliver the radionuclide metal chelate to a desired target site (e.g., target cells) in vitro or in vivo. Examples of targeting molecules include, but are not limited to, steroids, lymphokines, and those drugs and proteins that bind to a desired target site.

The targeting molecule may be a targeting protein, which is capable of binding to a desired target site. The term "protein" as used herein includes proteins, polypeptides, and fragments thereof. The targeting protein may bind to a receptor, substrate, antigenic determinant, or other binding site on a target cell or other target site. The targeting protein serves to deliver the radionuclide attached thereto to a desired target site in vivo. Examples of targeting proteins include, but are not limited to, antibodies, hormones, fibrinolytic enzymes, biologic response modifiers, and fragments thereof which are effective for targeting. In addition, other polymeric molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to bind to the target site) is retained. The proteins may be modified by using various genetic engineering or protein engineering techniques.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05, reactive with time 250 kilodalton human melanoma-associated proteoglycan; and NR-LU-10, reactive with a pancarcinoma glycoprotein. The antibody employed in the present invention may be an intact (whole) molecule, a fragment thereof, or a functional equivalent thereof (e.g., single chain equivalents comprising an antigen binding site). Examples of antibody fragments are F(ab')$_2$, Fab', Fab, and F$_v$ fragments, which may be produced by conventional methods or by genetic or protein engineering.

The chelating compounds of the present invention are radiolabeled, using conventional procedures, with any of a variety of radionuclide metals to form the corresponding radionuclide metal chelates. These radionuclide metals include, but are not limited to copper (e.g., $^{67}$Cu and $^{64}$Cu); technetium (e.g., $^{99m}$Tc); rhenium (e.g., $^{186}$Re and $^{188}$Re); lead (e.g., $^{212}$Pb); bismuth (e.g., $^{212}$Bi); palladium (e.g., $^{109}$Pd); and rhodium (e.g., $^{105}$Rh). Methods for preparing these isotopes are known. Molybdenum/technetium generators for producing $^{99m}$Tc are commercially available. Procedures for processing $^{186}$Re include the procedures described by Deutsch et al., (*Nucl. Med. Biol.* Vol. 13:4:465–477, 1986) and Vanderheyden et al. (*Inorganic Chemistry*, vol. 24:1666–1673, 1985), and methods for production of $^{188}$Re have been described by Blachot et al. (*Intl. J. of Applied Radiation and Isotopes* vol. 20:467–470, 1969) and by Klofutar et al. (*J. of Radioanalytical Chem.*, vol. 5:3–10, 1970). Production of $^{109}$Pd is described in Fawwaz et al., *J. Nucl. Med.* (1984), 25:796. Production of $^{212}$Pb and $^{212}$Bi is described in Gansow et el., *Amer. Chem. Soc. Symp. Ser.* (1984), 214:215–217, and Kozah et el., *Proc. Nat'l. Aced Sci.* USA (January 1986) 83:474–478. $^{99m}$Tc is preferred for diagnostic use, and the other radionuclides listed above have therapeutic use.

The radionuclide advantageously is in chelatable form when reacted with the protein-chelating compound conjugates of the invention. In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous aseorbate) and many others. Sodium pertechnetate (i.e., $^{99m}$TcO$_4$—which is in the +7 oxidation level) or sodium perrhenate (i.e., $^{188}$ReO$_4$—, $^{186}$ReO$^4$—) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene disphosphonate, glyceric acid, glycolic acid, tartaric acid, mannitol, oxalic acid, malonic acid, succinic acid, bicine, malic acid, N,N'-bis(2-hydroxy ethyl) ethylene diemine, citric acid, ascorbic acid and gentisic acid. Good results are obtained using gluconic acid or glucoheptonic acid as the technetium-complexing agent and citric acid for rhenium. When the radionuclide in the form of such an exchange complex is reacted with the chelating compounds of the invention (which are attached to a targeting molecule such as a protein), the radionuclide will transfer to these compounds which bind the radionuclide more strongly to form chelates of the invention. Radionuclides in the form of such exchange complexes also are considered to be in "chelatable form" for the purposes of the present invention.

Chelates of $^{212}$Pb, $^{212}$Bi, $^{103}$Rh, and $^{109}$Pd may be prepared by combining the appropriate salt of the radionuclide with the chelating compound and incubating the reaction mixture at room temperature or at higher temperatures. It is not necessary to treat the lead, bismuth, rhodium, palladium, and copper radioisotopes with a reducing agent prior to chelation, as such isotopes are already in an oxidation state suitable for chelation (i.e., in chelatable form).

The specific radiolabeling reaction conditions may vary somewhat according to the particular radionuclide and chelating compound involved. When the chelating compound is attached to a targeting protein prior to radiolabeling, the radiolabeling reaction is conducted under physiologically acceptable conditions to avoid denaturing or otherwise damaging the protein.

The present invention also provides a method for radiolabeling targeting proteins by attaching a chelating compound of formula I to the protein, then reacting the compound with a radionuclide metal. In one embodiment of the invention, the reaction of a chelating compound of the present invention with a protein is conducted at a pH of about 6–8, which is believed to favor reaction of hydroxyl groups on serine residues of the protein with the chelating compound. Alternatively, the reaction may be conducted at a pH of about 8–10 to favor reaction of the reagent with epsilon amines of lysine residues on the protein. In either reaction, the ring of the chelating compound opens and the compound is attached to the protein. The subsequent radiolabeling reaction produces a radionuclide metal chelate attached to the protein. Details of these reactions are presented in the examples below. The secondary sulfhydryls of the chelating compounds of the present invention may contribute to decreased aggregation. Aggregation is a problem with radiolabeled proteins produced using certain other procedures and reagents.

While not wishing to be bound by theory, the radionuclide metal is believed to bond to at least three (probably three or four) atoms of the chelating compound. Two of the atoms are the sulfur atoms shown in formula I, and the other atom(s) bonded to the radionuclide metal will vary depending on whether X represents oxygen, sulfur, or nitrogen-containing groups, and whether the reagent reacted with a lysine or serine residue of the protein. The five-membered rings of the chelate are believed to enhance the stability thereof.

The radiolabeled targeting molecules of the present invention have use in diagnostic and therapeutic procedures, both for in vitro assays and for in vivo medical procedures. The radiolabeled molecules may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting molecule for the target site of interest, and any cross-reactivity of the targeting molecule with normal tissues. Appropriate dosages may be established by conventional procedures and a physician skilled in the field to which this invention pertains will be able to determine a suitable dosage for a patient. A diagnostically effective dose is generally from about 5 to about 35 and typically from about 10 to about 30 mCi per 70 kg body weight. A therapeutically effective dose is generally from about 20 mCi to about 300 mCi. For diagnosis, conventional non-invasive procedures (e.g., gamma cameras) are used to detect the biodistribution of the diagnostic radionuclide, thereby determining the presence or absence of the target sites of interest (e.g., tumors).

The following examples are presented to illustrate certain embodiments of the invention, and are not to be construed as limiting the scope of the present invention.

EXAMPLE I Synthesis of S,S'-isopropylidene 2,3-dimercapto-succinic anhydride The following synthesis procedures may be represented by the following reaction scheme:

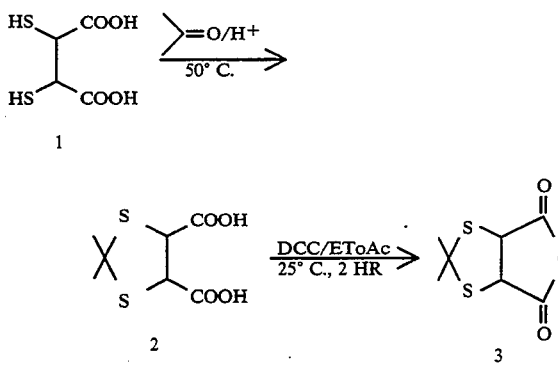

S,S'-isopropylidene 2,3-dimercaptosuccinic acid (2)

To 1.0 g of mego 2,3-dimercaptosuccinic acid (DMSA, 1) 50 mL anhydrous acetone followed by 0.3 mL (6 drops) perchloric acid were added. The heterogeneous suspension was heated at 50° C. for 2 hours. Solvent from the clear light golden yellow solution was removed under reduced pressure. To the dried residue 50 mL water was added and extracted with ethyl acetate three times, each time with 100 mL. The combined ethyl acetate extracts were dried over anhydrous sodium sulfate and the solvent was removed in vacuo. The dry solid was dissolved in ether and the compound was precipitated by the addition of petroleum ether. The solid was filtered to give 0.9 g (74%) of 2 as a white compound which could be recrystallized from $CHCl_3$/hexane to give crystals. MP 158°-160° C. $^1$NMR ($d_6$ acetone) $\delta$4.85 (S, 2H), $\delta$1.8, 1.9 (2S, 6H).

S,S'-isopropylidene 2,3-dimercaptosuccinic anhydride (3)

To 0.8 g (3.6 mmol) of S,S'-isopropylidene 2,3-dimercaptosuccinic acid (2), 10 mL of ethyl acetate was added. To this solution with stirring was added a solution of 1,3-dicyclohexylcarbodiimide 0.82 g (0.396 mmol) in 10 mL ethyl acetate. After stirring the reaction mixture at room temperature for 2 hours, tile reaction mixture was filtered to remove the dicyclohexylurea by-product of the reaction. Removal of the solvent from the filtrate left a white solid. Recrystallization from ether and petroleum ether gave 0.52 g (71%) of S,S'-isopropylidene 2,3-dimercaptosuccinic anhydride (3). The crude product was purified by sublimation, m.p. 141°-142° C. $^1$H NMR ($d_6$ acetone) $\delta$5.5 (S, 2H) $\delta$1.8 (S, 6H). Compound 3 is a chelating compound of the present invention (also referred to as a ligand elsewhere herein).

EXAMPLE II

Conjugation of Chelates Comprising Anhydride to an Antibody

The antibody used for derivatization was a monoclonal antibody fragment designated NR-LU-10 Fab, a murine antibody specific for human carcinoma surface antigen. The antibody is functionalized by dissolving the ligand, S,S'-isopropylidene 2,3-dimercaptosuccinic anhydride (compound 3 prepared in Example 1), in DMF during derivatization with 70:1 molar offering of ligand to antibody. 100 µL of 20 mg/mL NR-LU-10 Fab in phosphate buffered saline was mixed with 300 µL of 0.2M phosphate buffer, pH 7.9. To the buffered antibody solution, 30 µL of 2.0 mg/mL ligand solution in DMF was added. The reaction mixture was incubated at room temperature for 1 hour. Reaction at a pit of between 6 and 8 is believed to favor reaction of serine residues of the antibody with the ligand.

The resulting antibody-chelating compound conjugate was purified by size exclusion chromatography using a Sephadex G25 (PD-10) column equilibrated with 0.2M sodium acetate buffer, pH 5.0. The 2.4–4.8 mL fractions off the PD-10 column were collected and used for radiolabeling with Tc-99m.

The antibody-chelating compound conjugate is believed to have the following structure:

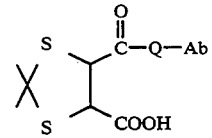

wherein Ab represents the antibody fragment and Q is an oxygen atom derived from the hydroxyl group of a serine residue on the antibody fragment. If the reaction had been conducted at a pH between 8 and 10 (believed to favor reaction of the ligand's ring with lysine rather than serine), then Q would represent

derived from a primary amine on a lysine residue.

In other conjugates of the present invention, any of the sulfur-protecting groups described above may replace the thioacetal group used in this example. The protecting group(s) stabilize the compound, e.g., by minimizing oxidation and reactivity with other molecules that can be a problem with unprotected sulfhydryl groups. However, if removal of the sulfur protecting groups is desired (e.g., just prior to radiolabeling), then a hydrogen atom will be attached to each of the two sulfur atoms shown. Likewise, the antibody fragment may be replaced by other targeting proteins.

EXAMPLE III

Tc-99m Radiolabeling of Antibody-Ligand Conjugate

To 100 µL of a solution containing 5 mg of sodium gluconate and 0.1 mg of stannous chloride in water, 1.0 mL of $^{99m}TcO_4$ (pertechnetate) was added. After incubation at room temperature for 1 minute to form $^{99m}Tc$-gluconate, 200 µL of the $^{99m}Tc$-gluconate solution was mixed with 525 µL of freshly prepared PD-10 purified antibody-ligand conjugate (about 0.44 mg antibody-ligand conjugate prepared in Example II). The reaction mixture was incubated at 37° C. for 15 minutes. The percentage of the Tc-99m from Tc-gluconate bound to the antibody-ligand conjugate was determined by standard instant thin layer chromatography (ITLC) in 12% trichloroacetic acid as a developing solvent. The percentage protein bound by ITLC was 78. The native antibody fragment underivatized with ligand was used as a control; Tc-99m uptake was 6.5%. The control experiment is an indication that the Tc-99m uptake by the antibody-ligand conjugate is specific for the ligand and that non-specific Tc-99m uptake is minimal.

EXAMPLE IV

Re-188 Radiolabeling of Antibody-Ligand Conjugates

The same chelating compound may be radiolabeled with $^{188}Re$ by a procedure similar to the $^{99m}Tc$ labeling procedure. Sodium perrhenate produced from a W-188/Re-188 research scale generator is combined with citric acid (a preferred complexing agent for $^{188}Re$), a reducing agent, and preferably gentisic acid and lactose. The resulting $^{188}Re$-citrate exchange complex is reacted with an antibody-ligand conjugate as described for the $^{99m}Tc$ procedure. A Sephadex G-25 column may be used to purify the radiolabeled antibody.

EXAMPLE V

Synthesis of S,S'-isopropylidene 2,3-dimercaptosuccinimide

S,S'-isopropylidene 2,3-dimercaptosuccinic anhydride (compound 3, prepared in Example I) is heated by a conventional method with an excess strong ammonia solution in a sealed tube reaction under pressure to give S,S'-isopropylidene 2,3-dimercaptosuccinimide, compound 4, in high yield, as shown:

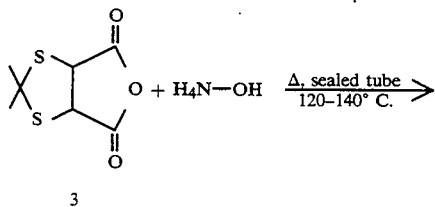

Compound 4 is attached to an antibody or other targeting protein and radiolabeled with $^{99m}Tc$ or $^{188}Re$ using the procedures described in Examples II–IV.

EXAMPLE VI

Synthesis of S,S'-isopropylidene 2,3-dimercapto-succinocyanimide

The reactivity of compound 4 (prepared in Example V) towards nucleophiles may be increased by replacing the imide proton with an electron withdrawing functionality such as —NO₂ or —CN (e.g., compound 5, prepared as follows).

S,S'-isopropylidene 2,3-dimercaptosuccinic anhydride 3 is heated with an excess cyanamide solution in polar solvents like dimethylformamide, dimethylsulfoxide, acetonitrile etc. to afford S,S'-isopropylidene 2,3-dimercaptosuccinocyanimide 5 in good yields.

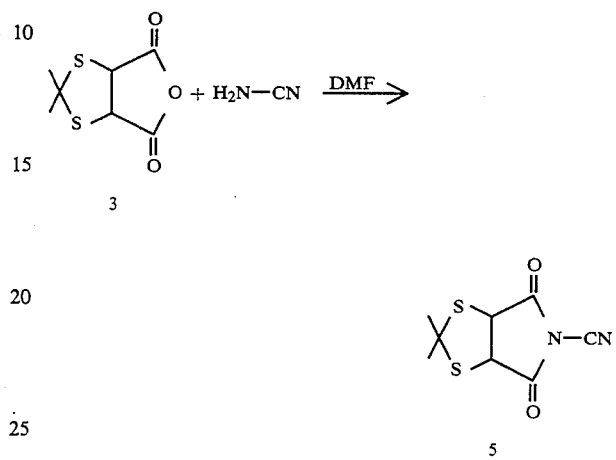

Compound 5 is attached to an antibody or other targeting protein and radiolabeled with $^{99m}Tc$ or $^{188}Re$ using the procedures described in Examples II–IV.

EXAMPLE VII

Synthesis of S,S'-isopropylidene 2,3-dimercaptothiosuccintc anhydride

S,S'-isopropylidene 2,3-dimercaptosuccinic acid 2 is refluxed with excess phosphorus pentasulfide in toluene by a conventional method to convert the carboxylic acids to thioacid moieties 6. The isopropylidene 2,3-dimercaptothiosuccinic acid is then dehydrated to a corresponding thiosuccinic anhydride 7 in ethyl acetate, methylene chloride or tetrahydrofuran solvent using dicyclohexylcarbodiimide as a coupling agent.

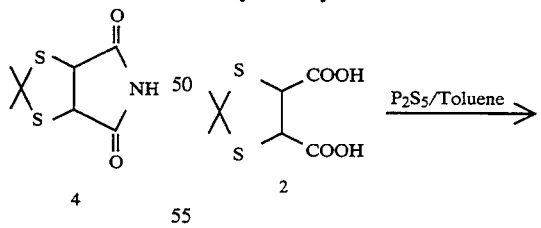

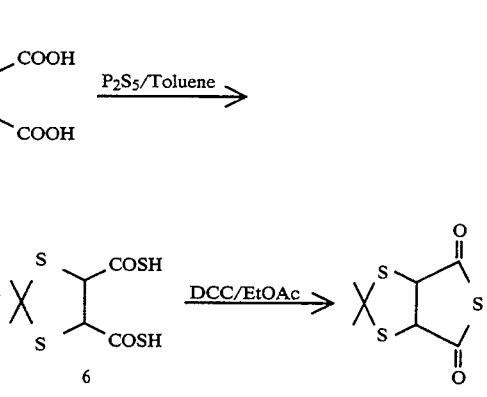

Compound 7 is attached to an antibody or other targeting protein and radiolabeled with $^{99m}Tc$ or $^{188}Re$ using the procedures described in Examples II–IV.

EXAMPLE VIII

Preparation of meso 2,3-bis S-(1-ethoxyethyl) dimercapto succinic acid (9a)

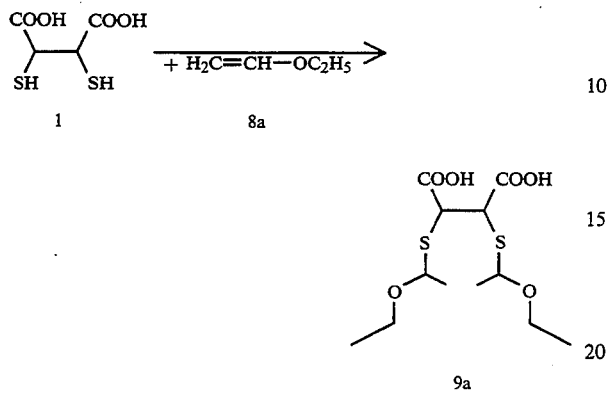

A solution of meso 2,3-dimercaptosuccirlic acid (4.55 g, 25 mmol) in 50 mL dichloromethane or tetrahydrofuran or other similar aprotic solvents containing p-toluene-sulfonic acid monohydrate (0.048 g, 0.252 mmol) is cooled to −18° to −25° C. with constant stirring. Ethyl vinyl ether (4.8 mL, 50 mmol) in 50 mL dichloromethane or other aprotic solvents is added dropwise to the cold solution over a period of 1.5 to 2 hours. The stirring is continued for an additional 30 minutes with the temperature maintained in the −18° to −25° C. range. Then 20 mL of pH 7 phosphate buffer is added, and time reaction mixture is allowed to warm with stirring for 10 to 15 minutes. The reaction mixture is then poured into a flask containing 100 mL of ethyl acetate and 25 mL of deionized water. The layers are separated and tile aqueous portion is extracted three times, each time with 50 mL ethyl acetate. The organic layers are combined, washed with water and than brine. The washed ethyl acetate extract is then dried over anhydrous sodium sulfate. Removal of the solvent gives 2 to 3 g of bis S-(1-ethoxyethyl) 2,3-dimercaptosuccinic acid. The material is used without further purification.

In similar reactions, meso 2,3-dimercaptosuccinic acid is reacted with 8b and 8c to give 9b and 9c respectively.

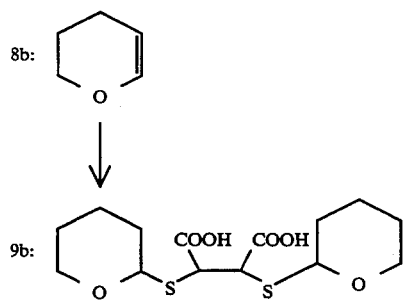

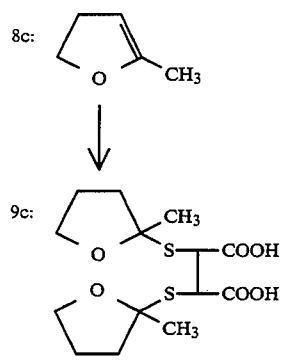

Preparation of meso bis S-(1-ethoxyethyl) 2,3-dimercapto-succinic anhydride (10)

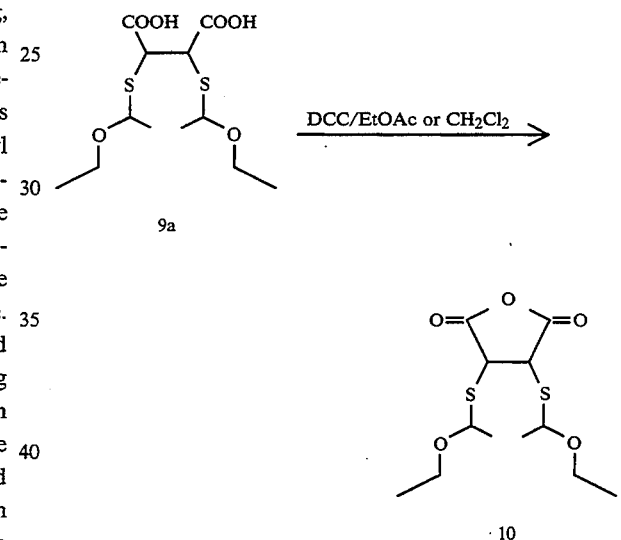

The ligand, meso bis S-(1-ethoxyethyl) 2,3-dimercaptosuccinic anhydride (10) is prepared by stirring 9a with 1.3 molar equivalents of 1,3-dicyclohexylcarbodiimide in methylene chloride, ethyl acetate or dry tetrahydrofuran at room temperature for 15-20 hours. The dicyclohexylurea is then removed by filtration, and the resulting liquid is concentrated in vacuo to yield 10 in good yield. Final purification of compound 10 is accomplished by flash chromatography or sublimation. Compounds 9b or 9c may be substituted for 9a in this reaction to give anhydrides similar to 10 but having the different hemithioacetal sulfur protecting groups shown in 9b and 9c. Compound 10 is attached to an antibody or other targeting protein and radiolabeled with $^{99m}$Tc or $^{188}$Re using the procedures described in Examples II--IV.

EXAMPLE IX

Cyclic ortho thioesters of meso 2,3.-dimercapto-succinic acids

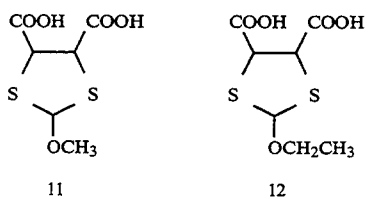

11  12

Compounds 11 and 12 are prepared by reaction at 0° C.-50° C. of meso 2,3-dimercaptosuccinic acid with 8 large excess ($\geq$10 molar excess) of trimethyl or triethyl orthoformate respectively in the absence and presence, respectively, of a cosolvent like methylene chloride, tetrahydrofuran or other similar aprotic solvents using strong acid catalysts such as perchloric acid or p-toluenesulfonic acid.

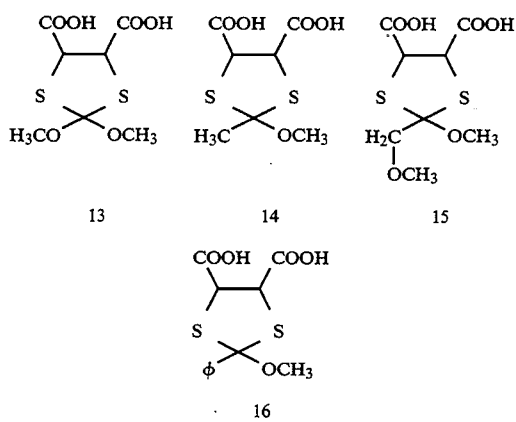

13  14  15

16

In similar reactions, meso 2,3-dimercaptosuccinic acid is reacted with tetramethylorthocarbonate (TsOH/dioxane) to yield compound 13 in good yield. Compound 14 is prepared by acid-catalyzed transketalization [MeC-(OMe),, TsOH] in 50% yield. Compound 15 is prepared by acid-catalyzed transketalization [MeOCH$_2$C(OMe)$_3$, methanesulfonic acid] in DMF solvent at 20° C. for 3–7 hours. The methoxy benzylidene ortho ester, 16 is prepared by conditions similar to those described for compound 14.

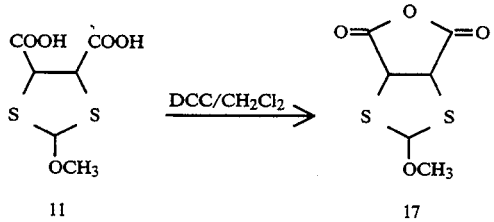

11  17

Meso S,S'-methylorthothioformate of 2,3-dimercaptosuccinic anhydride (17) is prepared by stirring meso S,S'-methylorthothioformyl 2,3-dimercaptosuccinic acid (11) with 1.3 molar equivalents of 1,3-dicyclohexylcarbodiimide (DCC) in methylene chloride at room temperature for 15–20 hours. The progress of the reaction is followed by thin layer chromatography. The resulting precipitate of dicyclohexyl urea is removed by filtration. Time filtrate was concentrated in vacuo to yield 17 as a crude product. The final purification of the meso S,S'-methylorthothioformyl 2,3-dimercaptosuccinic anhydride 17 is accomplished by sublimation.

Compounds 12–16 may be substituted for compound 11 in the above procedure to prepare time corresponding anhydrides. Compounds 11–16 differ in the particular thioacetal sulfur protecting group employed, with compound 11 being preferred.

EXAMPLE X

Preparation of Radiolabeled Antibodies Conjugation to Antibodies, Whole IgG or Fragments Thereof Though the compound 17, meso S,S'-methylorthothioformyl 2,3-dimercaptosuccinic anhydride, will conjugate to a number of nucleophilic groups on the antibody, a higher pH, favoring lysine residues, would be preferred in order to maintain sulfur protection on the heterocyclic ring. The sulfur-containing heterocyclic ring is subject to acid-catalyzed hydrolysis that would produce free thiols. When certain other radiolabeling techniques involving molecules with unprotected sulfhydryls are employed, the sulfhydryls (thiols) have been postulated to function as bridges for Tc-induced aggregate antibody formation.

Hence, to 100 $\mu$L of 20 mg/mL Fab antibody fragment in Phosphate buffered saline, 300 $\mu$L of 0.2M carbonate, pH 9–10 is added followed by addition of 30 $\mu$L of 2.0 mg/mL ligand 17 in DMSO, DMF or other appropriate polar solvent. The reaction is allowed to incubate for 1 hour at room temperature to allow for completion of aminolysis with lysine residues at the 70:1 ligand to antibody molar offering. The antibody is subsequently purified of unreacted hydrolyzed ligand via size exclusion chromatography using a PD-10 Sephadex (Pharmacia) column which is pre-equilibrated in PBS of pH 7.7. The appropriate conjugate is collected in the 2.4 to 4.8 mL fraction.

Whole antibody, other antibody fragments, or other proteins may be substituted for the Fab antibody fragment in this procedure.

Tc-99m Labeling of Antibody Ligand 17 Conjugate

1. Preparation of Intermediate Tc-Gluconate Exchange Complex

To 1.0 mL of sodium pertechnetate Tc-99m of appropriate specific activity is added 100 $\mu$L of stannous gluconate (of 100 $\mu$g stannous chloride, 1–2.5 mg sodium gluconate $\approx$pH 6). Incubate the reaction mixture at room temperature for 1 minute to effect technetium reduction from +7 oxidation state and chelation with Tc$^{+5}$ to form Tc-gluconate.

2. Preparation of Tc-Labeled Antibody Conjugate

To 200 $\mu$g of the above PD-10 purified ligand-antibody conjugate, add 100 $\mu$L of 0.2M phosphate buffer pH 5.0–8.5 followed by 200 $\mu$L of Tc-gluconate solution. Incubate the reaction mixture at 37 ° C. for $\leq$30 minutes to allow for transfer of Tc$^{+5}$ from Tc-gluconate into the ligand conjugated to the antibody species. Care should be taken to minimize deblocking of sulfhydryls of the ligand, which may lead to undesirable antibody aggregation with technetium serving as a bridge between multiple ligands on different antibody moieties.

Labeling with rhenium may be accomplished by the procedures described in Example IV.

EXAMPLE XI

Synthesis of meso S,S'-isopropylidene 2,3-dimercapto hemisuccinic acid carboxamide The synthesis procedure is depicted in the following reaction scheme:

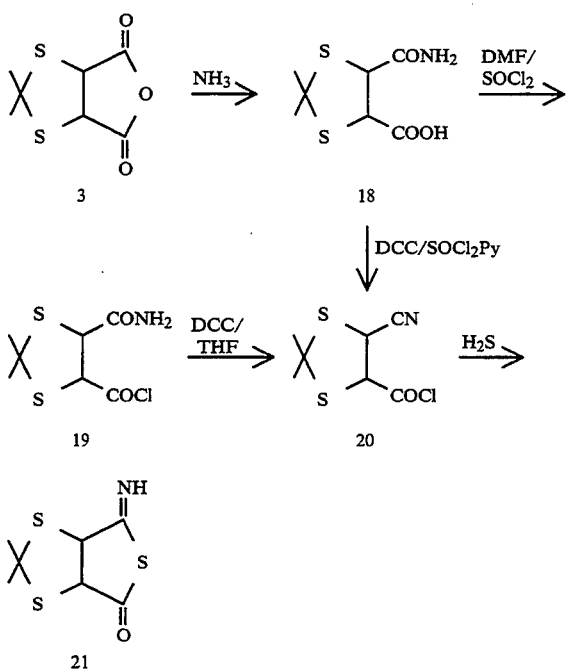

Meso S,S'-isopropylidene 2,3-dimercaptosuccinic anhydride (compound 3 prepared in Example I) is dissolved in methylene chloride, or ethyl acetate or tetrahydrofuran or similar aprotic solvents and cooled. Into the cold solution, liquid ammonia is bubbled and the solution is warmed up slowly to room temperature. The desired half acid and half carboxamide 18 is precipitated from the solution. The precipitate is filtered and recrystallized.

Compound 18 is dissolved in anhydrous DMF and an excess of thionyl chloride (10 molar equivalents) is added and stirred at room temperature for 12 to 15 hours. The solvent from the reaction mixture is removed under reduced pressure and dried to yield compound 19 in good yield. The dry compound 19 is redissolved in tetrahydrofuran and 1.1 molar equivalents of 1,3-dicyclohexylcarbodiimide is added. The reaction mixture is stirred at room temperature for 12-15 hours. The dicyclohexyl urea is removed by filtration and the solvent from reaction mixture is removed under reduced pressure to yield nitrile 20 in good yield. Alternatively compound 20 is prepared in one step by reaction of compound 18 with 1,3-dicyclohexyl carbodiimide and thionyl chloride in pyridine solution at room temperature. Compound 20 is dissolved in aprotic solvent and reacted with excess molar concentration of hydrogen sulfide. After 1-2 hours stirring at room temperature, the solvent is removed from the reaction mixture under reduced pressure to obtain compound 21 in good yield. The crude compound 21 is recrystallized or purified by flash chromatography.

EXAMPLE XII

Conjugation to Antibodies, Whole IgG or Fragments 0.3 mL of 0.2M carbonate, pH 9-pH 10 is added to 0.1 mL of 20 mg/mL antibody Fab fragment in phosphate buffered saline, followed by addition of 35 μL of 2.0 mg/mL of ligand 21 in DMF or DMSO or other appropriate polar solvent. The reaction is allowed to incubate for 1 hour at room temperature to allow for completion of aminolysis with lysine residues at the 75:1 ligand to antibody molar offering. The antibody is subsequently cleaned up of unreacted hydrolyzed ligand via size exclusion chromatography using a PD-10 Sephadex (Pharmacia) column which is pre-equilibrated with PBS of pH 7.7. The appropriate conjugate is collected in the 2.4-4.8 mL fraction.

Tc-99m radiolabeling of antibody-ligand 21 conjugate is carried out by the exact procedure described for antibody-ligand 17 conjugate radiolabeling.

What is claimed is:

1. A compound of the formula:

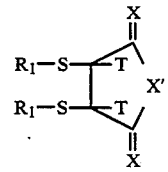

wherein:
  each X is independently chosen from S, NH, or $NR_2$, X' is independently chosen from S, NH or $NR_2$, wherein $R_2$ represents a substituent selected from nitrogen protecting groups and electron withdrawing groups;
  $R_1$ represents a sulfur protecting group, wherein each $R_1$ is a separate protecting group or the two $R_1$ symbols are taken together to represent a single protecting group; and
  each T is independently chosen from hydrogen, lower alkyl groups of from 1 to about 6 carbon atoms, electron withdrawing groups, and lower alkyl groups of from 1 to about 6 carbon atoms substituted with electron withdrawing group(s).

2. A compound of the formula:

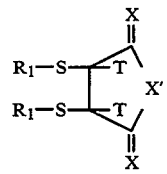

wherein:
  each X is O, X' is independently chosen from S or NH;
  $R_1$ represents a sulfur protecting group, wherein each $R_1$ is a separate protecting group or the two $R_1$ symbols are taken together to represent a single protecting group; and
  each T is independently chosen from hydrogen, lower alkyl groups of from 1 to about 6 carbon atoms, electron withdrawing groups, and lower alkyl groups of from 1 to about 6 carbon atoms substituted with electron withdrawing group(s).

3. The compound of claim 1 or claim 2 wherein each T is hydrogen.

4. The compound of claim 1 or claim 2 wherein each —S—$R_1$ group is independently selected from S-acyl groups of the formula

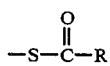

wherein R is an alkyl or aryl group; hemithioacetals; and S-acetamidomethyl groups.

5. The compound of claim 1 or claim 2 wherein the two $R_1$ symbols are taken together to represent a single protecting group which, together with the two sulfur atoms bonded thereto, is a thioacetal group.

6. A compound of the formula:

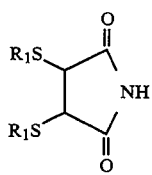

wherein each $R_1$ represents a separate protecting group or the two $R_1$ symbols are taken together to represent a single protecting group.

7. A compound of the formula:

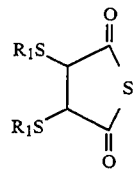

wherein each $R_1$ represents a separate protecting group or the two $R_1$ symbols are taken together to represent a single protecting group.

8. A compound of the formula:

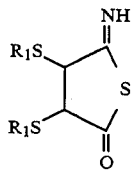

wherein each $R_1$ represents a separate protecting group or the two $R_1$ symbols are taken together to represent a single protecting group.

9. The compound of claim 6, 7, or 8 wherein each —S—$R_1$ group represents a separate hemithioacetal group.

10. The compound of claim 6, 7, or 8 wherein the single protecting group attached to both sulfur atoms is a thioacetal of the following formula, wherein the two sulfur atoms of the compound are shown attached to the protecting group:

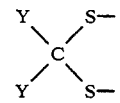

wherein each Y is independently chosen from hydrogen, an aromatic ring, a methyl group, an ethyl group, and alkoxy groups comprising from one to two carbon atoms.

* * * * *

UNITED STATES PATENT AND TRADEMARK OFFICE
CERTIFICATE OF CORRECTION

PATENT NO. : 5,399,710

DATED : March 21, 1995

INVENTOR(S) : Kasina et al.

It is certified that error appears in the above-indentified patent and that said Letters Patent is hereby corrected as shown below:

In column 5, line 31, delete "time" and substitute therefor --the--.

In column 6, line 56, delete "time" and substitute therefor --the--.

In column 7, line 20, delete "*Aced*" and substitute therefor --*Acad.*--.

In column 7, line 57, delete "diemine" and substitute therefor --diamine--.

In column 9, line 33, delete "mego" and substitute therefor --meso--.

In column 9, line 49, delete "$^1$NMR" and substitute therefor --$^1$H NMR--.

In column 9, line 58, delete "tile" and substitute therefor --the--.

In column 10, line 18, delete "pit" and substitute therefor --pH--.

In column 12, line 36, delete "2,3-dimercaptothiosuccintc" and substitute therefor --2,3-dimercaptothiosuccinic--.

In column 13, line 24, delete "2,3-dimercaptosuccirlic" and substitute therefor --2,3-dimercaptosuccinic--.

UNITED STATES PATENT AND TRADEMARK OFFICE
CERTIFICATE OF CORRECTION

PATENT NO. : 5,399,710
DATED : March 21, 1995
INVENTOR(S) : Kasina et al.

It is certified that error appears in the above-indentified patent and that said Letters Patent is hereby corrected as shown below:

In column 13, line 42, delete "tile" and substitute therefor --the--.

In column 13, line 45, delete "than" and substitute therefor --then--.

In column 15, line 3, delete "2,3.-dimercapto" and substitute therefor --2,3-dimercapto--.

In column 15, line 16, delete "8" and substitute therefor --a--.

In column 15, line 44, delete "(OMe),," and substitute therefor --(OMe)$_3$,--.

In column 16, line 1, delete "Time" and substitute therefor --The--.

In column 16, line 6, delete "time" and substitute therefor --the--.

Signed and Sealed this

Nineteenth Day of December, 1995

Attest:

BRUCE LEHMAN

Attesting Officer

Commissioner of Patents and Trademarks